United States Patent [19]

Ahlstrom, Jr.

[11] 3,996,300
[45] Dec. 7, 1976

[54] REMOVAL OF CHLORAL FROM EFFLUENT GAS OF 1,2-DICHLOROETHANE SYNTHESIS

[75] Inventor: Ross C. Ahlstrom, Jr., Bay City, Tex.

[73] Assignee: The Dow Chemical Company, Midland, Mich.

[22] Filed: Mar. 18, 1976

[21] Appl. No.: 668,009

[52] U.S. Cl. .......................................... 260/652 P
[51] Int. Cl.$^2$ ........................................ C07C 17/38
[58] Field of Search ................................ 260/652 P

[56] References Cited

UNITED STATES PATENTS 3,378,597   4/1968   Dehn et al. ................... 260/652 P

*Primary Examiner*—D. Horwitz
*Attorney, Agent, or Firm*—A. Cooper Ancona

[57] ABSTRACT

In the manufacture of ethylene dichloride by the oxychlorination of ethylene, chloral is a highly corrosive by-product which must be removed prior to condensing the product gases in order to avoid damage to the condenser. The effluent from the oxychlorination reactor is quenched by a counter-current flow of an aqueous solution of alkali or alkaline earth metal hydroxides, carbonates, bicarbonates or borates maintained at a pH of about 8–9. This enables the chloral to react without an appreciable loss of carbon dioxide from the non-condensible product gases which are employed as recycle diluent in the process.

3 Claims, No Drawings

REMOVAL OF CHLORAL FROM EFFLUENT GAS OF 1,2-DICHLOROETHANE SYNTHESIS

BACKGROUND OF THE INVENTION

In the manufacture of ethylene dichloride (1,2-dichloroethane or EDC) by oxychlorination of ethylene, chloral (trichloroacetaldehyde) is a by-product which is highly corrosive and must be removed prior to condensation of the reactor effluent. U.S. Pat. No. 3,488,398, assigned to B. F. Goodrich, to a method of preparing EDC (1,2-dichloroethane) employs a hot quench (70°–100° C) under pressure to remove excess HCl, most of the chloral and some water of reaction; the remaining gases are cooled to 0°–40° C to condense the remaining water and EDC. The chloral is decomposed in the hot quench by raising the pH of water to about 10 by adding an alkali or alkaline earth oxide, hydroxide or other alkaline substance to the quench water. The process for making EDC described therein is a single-pass non-recycle process.

The present invention, to the contrary, involves recycle of the non-condensible gases which includes $CO_2$. Thus, it is important to retain the $CO_2$ in th system.

SUMMARY OF THE INVENTION

In the process of making ethylene dichloride (1,2-dichloroethane) from ethylene, HCl and $O_2$ over a copper chloride catalyst and wherein enriched air or pure oxygen is employed as the source of oxygen and wherein the inert gases, namely $CO_2$ and CO which together constitute over 75 mole percent of the inerts, are employed as recycle it is important, when removing the chloral from the system, that a minimum amount of $CO_2$ be removed so that the desired volume of recycle gas is maintained. It has now been discovered that maintaining the effluent of the aqueous quench system at a pH within the range of from about 8.0 to 9.0 accomplishes the decomposition of the chloral and at the same time minimizes the loss of $CO_2$ from the inert gases employed thereafter as recycle.

While it is known to employ caustic and other alkaline compounds in the aqueous quench to remove chloral, the pH of 10 as taught in U.S. Pat. No. 3,488,398 will absorb the $CO_2$ in the effluent gases. This is wasteful of the alkalinity necessary to decompose the chloral while at the same time it removes a necessary component from the recycle gas stream. The present process, by operating within a narrow pH range, accomplishes the removal and decomposition of chloral while minimizing the absorption of $CO_2$, thus maintaining the volume of recycle diluent gases.

DETAILED DESCRIPTION OF THE INVENTION

The quench solution is employed in a recycle, counter-current flow system in a packed column. The quench solution is introduced at the top of the column and the EDC process gas is introduced at the bottom of the column. The pH of the quench is measured after it exits from the column. Additional quench solution is added as needed (as indicated by the pH measurement) and a level control is employed to remove the spent quench solution in a volume equal to that which is added to maintain the pH.

The solution employed for control of the pH of the quench normally contains from about 1 to about 1.5 weight percent caustic (NaOH) and up to about 0.5 weight percent $Na_2CO_3$. When the pH drops below about 8.0, more of the solution is added; while when it rises above about 8.5, the addition is halted. The following examples show the effect of adjusting the pH of the quench solution on the removal of chloral and absorption of $CO_2$.

Example 1

In the process of making EDC from ethylene, HCl and $O_2$ over an oxychlorination catalyst of $CuCl_2$ the effluent gases were passed into a counter-current flow of aqueous alkaline quench solution in a column packed with ¼-inch Intalox saddles to a height of 36 inches at a rate sufficient to give a contact time of 10 seconds. The pH of the quench effluent was 8.4. The composition of the gas stream before and after contacting is shown below:

| Effluent Components | Mole % before quench | Mole % after quench |
|---|---|---|
| EDC | 41.25 | 41.43 |
| $CO_2$ | 28.67 | 28.34 |
| $N_2$ | 29.96 | 30.09 |
| Chloral | 0.13 | — |
| Chloroform | — | 0.13 |

Examples 2–8

In like manner the $CO_2$ and chloral were measured after using quench solutions of various pH. The composition of the gas stream with respect to $CO_2$ and chloral was 28.67 and 0.13 mole percent, respectively, prior to the quench treatment. The following table shows the $CO_2$ and chloral remaining after treatment of the gas stream when employing solutions of various pH.

| Example | Component (mole %) $CO_2$ | chloral | pH |
|---|---|---|---|
| 2 | 28.67 | 0.011 | 7.2 |
| 3 | 28.45 | 0.003 | 7.8 |
| 4 | 28.07 | 0.000 | 8.0 |
| 5 | 27.78 | 0.000 | 8.3 |
| 6 | 27.59 | 0.000 | 8.6 |
| 7 | 26.95 | 0.000 | 9.3 |
| 8 | 14.79 | 0.000 | 11.0 |

As can be seen from the table above an operable range of pH of the quench is from about 7.8 to about 9.3, while the preferred range of pH is from about 8.0 to about 8.6.

I claim:

1. In a process wherein the effluent from an oxychlorination reactor employed in the manufacture of 1,2-dichloroethane is quenched to remove chloral therefrom by employing an aqueous alkaline quench solution, the improvement which comprises controlling the pH of the aqueous solution within the range of about 7.8 to about 9.3.

2. The process of claim 1 wherein the pH is within the range of about 8.0 to about 8.6.

3. A process for removing chloral from a recycle stream of an oxychlorination process for making ethylene dichloride, wherein said stream contains a major amount of carbon oxides which comprises quenching the effluent from the oxychlorination reactor by passing it through an aqueous quench tower in a counter-current manner, wherein an aqueous alkaline solution is employed and wherein the pH of said solution is maintained within the range of about 8.0 to about 9.0.

* * * * *